United States Patent
Yoshida et al.

(10) Patent No.: US 8,138,146 B2
(45) Date of Patent: Mar. 20, 2012

(54) ANTIVIRAL PEPTIDE AND ANTIVIRAL AGENT

(75) Inventors: Tetsuhiko Yoshida, Nagoya (JP); Nahoko Kobayashi, Nagoya (JP); Takanori Sato, Kawasaki (JP)

(73) Assignee: Toagosei Co., Ltd, Tokyo (JP)

( * ) Notice: Subject to any disclaimer, the term of this patent is extended or adjusted under 35 U.S.C. 154(b) by 602 days.

(21) Appl. No.: 12/280,701

(22) PCT Filed: Feb. 28, 2007

(86) PCT No.: PCT/JP2007/053738
§ 371 (c)(1),
(2), (4) Date: Aug. 26, 2008

(87) PCT Pub. No.: WO2007/099993
PCT Pub. Date: Sep. 7, 2007

(65) Prior Publication Data
US 2009/0258815 A1   Oct. 15, 2009

(30) Foreign Application Priority Data
Feb. 28, 2006   (JP) ................................ 2006-053816

(51) Int. Cl.
*C07K 14/00* (2006.01)
(52) U.S. Cl. ........................................ 514/3.7; 530/324
(58) Field of Classification Search .................. 514/3.7; 530/324
See application file for complete search history.

(56) References Cited

U.S. PATENT DOCUMENTS

| | | | |
|---|---|---|---|
| 5,827,891 A | 10/1998 | Dressman et al. | |
| 5,840,843 A | 11/1998 | Jiang et al. | |
| 6,468,969 B1 | 10/2002 | Rana et al. | |
| 6,482,412 B1 | 11/2002 | Tanaka et al. | |
| 2006/0057668 A1 | 3/2006 | Yoshida et al. | |

FOREIGN PATENT DOCUMENTS

| | | |
|---|---|---|
| CA | 2166374 | 7/1996 |
| WO | 9909056 | 2/1999 |
| WO | 0032629 | 6/2000 |
| WO | 0157072 | 8/2001 |

OTHER PUBLICATIONS

International Search Report for PCT/JP2007/053738 dated Apr. 17, 2007.
Mears, et al., Identification of Nuclear and Nucleolar Localization Signals in the Herpes Simplex Virus Regulatory ICP27, Journal of Virology, Feb. 1995, vol. 69, pp. 935-947.
Hibbard, et al., Arginine-Rich Regions Succeeding the Nuclear Localization Region of the Herpes Simplex Virus Type 1 Regulatory Protein ICP27 are Required for Efficient Nuclear Localization and Late Gene Expression, Journal of Virology, Aug. 1995, vol. 69, pp. 4656-4667.
Truant, et al., The Arginine-Rich Domains Present in Human Immunodeficiency Virus Type 1 Tat and Rev Function as Direct Importin B-Dependent Nuclear Localization Signals, Molecular and Cellular Biology, Feb. 1999, vol. 19, pp. 1210-1217.
Elfgang, et al., Evidence for Specific Nucleocytoplasmic Transport Pathways Used by Leucine-Rich Nuclear Export Signals, Proc. Natl. Acad. Sci. USA, May 1999, vol. 96, pp. 6229-6234.
Ho et al., Synthetic Protein Transduction Domains: Enhanced Transduction Potential In Vitro and In Vivo, Cancer Research, Jan. 2001, vol. 61, pp. 474-477.
Lengyel et al., Mapping of Functional Regions in the Amino-Terminal Portion of the herpes Simplex Virus ICP27 Regulatory Protein: Importance of the Leucine-Rich Nuclear Export Signal and RGG Box RNA-Binding Domain, Journal of Virology, Dec. 2002, vol. 76, pp. 11866-11879.
Loewen et al., A Conserved ER Targeting Motif in Three Families of Lipid Binding Proteins and in Opi1p Binds VAP, The EMBO Journal, 2003, vol. 22, pp. 2025-2035.
Liu et al., ZAP is a CRM1-Dependent Nucleocytoplasmic Shuttling Protein, Biochemical and Biophysical Research Communications, Jun. 2004, vol. 321, pp. 517-523.
Loewen et al., A Highly Conserved Binding Site in Vesicle-Associated Membrane Protein-Associated Protein (VAP) for the FFAT Motif of Lipid-Binding Proteins, Journal of Biological Chemistry, Apr. 2005, vol. 280, pp. 14097-14104.
Perry et al., Molecular Mechanisms and Regulation of Ceramide Transport, Biochimica Et Biophysica Acta, May 2005, vol. 1734, pp. 220-234.

*Primary Examiner* — David Lukton
(74) *Attorney, Agent, or Firm* — Turocy & Watson, LLP

(57) ABSTRACT

Disclosed is an antiviral agent comprising a non-naturally occurring, artificially synthesized peptide as the main ingredient. The antiviral agent comprises an antiviral peptide, wherein the antiviral peptide has at least one unit of an amino acid sequence constituted by at least five contiguous amino acid residues (which is known as a nuclear localization sequence (NLS)) or an amino acid sequence having a partial modification in the NLS and also having at least one unit of an amino acid sequence constituted by at least five contiguous amino acid residues (which is known as a nuclear export sequence (NES)) or an amino acid sequence having a partial modification in the NES.

4 Claims, No Drawings

ANTIVIRAL PEPTIDE AND ANTIVIRAL AGENT

This application is a national stage entry of PCT/JP2007/053738, filed Apr. 17, 2007, which claims foreign priority to JP 2006-053816, filed Feb. 28, 2006.

TECHNICAL FIELD

The present invention relates to an oligopeptide or a polypeptide having antiviral properties (hereinafter collectively referred to as "antiviral peptide") comprising an independent peptide chain that is not naturally occurring and to use thereof; in particular, it relates to an antiviral agent (antiviral composition) having such antiviral peptide as main component and to a preparation method therefor.

BACKGROUND ART

Since medical agents that are effective for preventing or curing a viral disease (antiviral agents) are limited, development of novel antiviral agents is actively progressing by a variety of approaches.

As one of such approaches, search for and development of naturally derived or artificially made antiviral peptides that may prevent or may decrease multiplication of virus are progressing. For instance, antiviral peptides discovered or developed so far are described in the following Patent Documents 1, 2 and 3.

Patent Document 1: International Publication WO 00/32629 Pamphlet

Patent Document 2: International Publication WO 00/52043 Pamphlet

Patent Document 3: International Publication WO 01/57072 Pamphlet

DISCLOSURE OF THE INVENTION

An object of the present invention is to design a novel antiviral peptide, which is a peptide that is different from existing antiviral peptides such as described in each of the above-mentioned patent references, and different from peptides existing in nature and functioning as antiviral peptides. In addition, another object of the present invention is to use the peptide disclosed herein for the purpose of suppressing viral multiplication. In addition, another object of the present invention is to provide a method for suppressing viral multiplication distinguished by the use of the peptide disclosed herein. In addition, another object is to prepare an antiviral peptide designed by the present invention to provide an antiviral agent (antiviral composition) having the peptide as main component. Further in addition, another object is to provide a polynucleotide coding for the antiviral peptide disclosed herein.

The antiviral agent (typically, a pharmacological composition that may be used in medical field or health field) provided by the present invention, having as main component a non-naturally occurring, artificially synthesized peptide having antiviral activity against at least one species of virus, contains an antiviral peptide having at least one unit (repeat) of an amino acid sequence composed of at least five contiguous amino acid residues known (understood) as nuclear localization sequence (NLS) or an amino acid sequence composed of a NLS that has been partially modified, and, at least one unit (repeat) of an amino acid sequence composed of at least five contiguous amino acid residues known (understood) as nuclear export signal sequence (NES) or an amino acid sequence composed of a NES that has been partially modified, and a pharmacologically acceptable carrier (including a variety of carriers and media; idem hereinafter).

The antiviral peptide contained in the antiviral agent disclosed herein is an antiviral peptide designed artificially using two species of amino acid sequence with different functions from one another. That is to say, the present inventors found that an artificially designed and synthesized peptide (refer to pamphlet of International Publication WO 03/91429, the entirety of which is incorporated herein by reference) had excellent antiviral properties, and reached completion of the present invention.

The antiviral peptide disclosed herein is a non-naturally occurring, artificially synthesized antiviral peptide having antiviral properties against at least one species of virus.

The antiviral peptide disclosed herein has, as a first amino acid sequence participating in the antiviral expression, one unit or two or more units of an amino acid sequence constituted by at least five contiguous amino acid residues known as nuclear localization sequence (nuclear localization signal sequence: NLS) or an amino acid sequence composed of a NLS that has been partially modified (hereinafter, sometimes collectively referred to as "NLS-related sequence"). NLS is a sequence that has been identified in a variety of species of living organisms and viruses, and is generally a partial amino acid sequence rich in basic amino acids present in a variety of polypeptides that translocate into the nucleus within a cell. For instance, the literature of R. Truant and B. R. Cullen (MOLECULAR AND CELLULAR BIOLOGY, volume 19 (2), 1999, pp. 1210-1217) describes an NLS present in the human immunodeficiency virus (HIV). The content of the literature in its entirety is incorporated herein by reference.

In addition, the antiviral peptide disclosed herein has, as a second amino acid sequence participating in antiviral expression, one unit or two or more units of an amino acid sequence constituted by at least five contiguous amino acid residues known as nuclear export signal sequence (nuclear export signal sequence: NES) or an amino acid sequence composed of a NES that has been partially modified (hereinafter, sometimes collectively referred to as "NES-related sequence"). NES is a sequence that has been identified in a variety of species of living organisms and viruses, and is generally a hydrophobic partial amino acid sequence comparatively rich in leucine residues present in a variety of polypeptides translocating outside of the nucleus (for instance ribonucleoproteins) within a cell. For instance, the literature of C. Elfgang, O. Rosorius, L. Hofer, H. Jaksche, J. Hauber and D. Bevec (PNAS, volume 96, 1999, pp. 6229-6234) describes a variety of NES's. The content of the literature in its entirety is incorporated herein by reference.

The present inventors found that a peptide chain designed to contain together the above-mentioned NLS-related sequence and NES-related sequence may exert a high antiviral activity (multiplication inhibition activity) against a variety of viruses, and reached completion of the present invention.

By having as main constitutive elements an NLS-related sequence and an NES-related sequence constructed each by at least five contiguous amino acid residues, the antiviral peptide disclosed herein may exert high antiviral activity against a variety of viruses capable of infecting humans and other mammals or avian.

Preferably, the at least one unit of NLS or modified sequence thereof and the at least one unit of NES or modified sequence thereof are positioned contiguously with respect to each other within the peptide chain of the antiviral peptide.

Such a sequence allows higher antiviral activity to be exerted.

Consequently, an antiviral agent containing such a peptide is one preferred mode of antiviral agent provided by the present invention.

In addition, preferably, the total number of amino acid residues constituting the peptide chain of the antiviral peptide is 30 or fewer. A peptide with a short chain length can be readily prepared for instance by a generic chemical synthesis method and purified, and at the same time is easily handled. Consequently, an antiviral agent containing such a peptide is one mode of antiviral agent desirable for in vivo and/or in vitro use provided by the present invention.

In addition, preferably, the NLS or modified sequence thereof contained in the antiviral peptide is a virus-derived NLS or modified sequence thereof. High antiviral activity may be obtained by having a virus-derived NLS-related sequence. Consequently, an antiviral agent containing such a peptide is one mode of preferred antiviral agent provided by the present invention.

For instance, having an amino acid sequence selected from the group consisting of SEQ ID No:1, SEQ ID No:2, SEQ ID No:3, SEQ ID No:4 and SEQ ID No:5 is desirable.

In addition, as another aspect, the present invention provides a method for preparing the antiviral agent disclosed herein. That is to say, the present invention provides a method for producing an antiviral agent having as main component a non-naturally occurring, artificially synthesized peptide having antiviral activity against at least one species of virus, comprising:

(a) designing a peptide chain having at least one unit of an amino acid sequence constituted by at least five contiguous amino acid residues known (understood) as nuclear localization sequence (NLS) or amino acid sequence composed of a NLS that has been partially modified, and, at least one unit of an amino acid sequence constituted by at least five contiguous amino acid residues known (understood) as nuclear export signal sequence (NES) or an amino acid sequence composed of a NES that has been partially modified, and (b) synthesizing an antiviral peptide composed of the designed peptide chain.

The antiviral agent of the present invention can be prepared by mixing with an adequate carrier (for instance physiological saline) an antiviral peptide obtained by synthesizing the peptide chain designed to contain an NLS-related sequence and an NES-related sequence in this way.

Preferably, the peptide chain is designed in such a way that the at least one unit of NLS or modified sequence thereof and at least one unit of NES or modified sequence thereof are positioned contiguously with respect to each other. This allows an antiviral agent that may exert higher antiviral activity to be provided.

In addition, preferably, the peptide chain is designed in such a way that the total number of amino acid residues constituting the peptide chain is 30 or fewer. This allows an antiviral agent with ease of handling and good liberty of use to be provided.

In addition, preferably, a virus-derived NLS or an modified sequence thereof is adopted as NLS or modified sequence thereof. This allows an antiviral agent having a higher antiviral activity to be provided. For instance, an amino acid sequence selected from the group consisting of SEQ ID No:1, SEQ ID No:2, SEQ ID No:3, SEQ ID No:4 and SEQ ID No:5 can be adopted as NLS-related sequence.

In addition the present invention provides a method for suppressing multiplication of virus (for instance influenza virus) whereby an antiviral composition containing any peptide disclosed herein is prepared, and the composition is administered to a patient or a subject. In other words, the present invention provides the use of any peptide disclosed herein for suppressing multiplication of a virus.

| <Sequence List Free Text> | |
|---|---|
| SEQ ID No: 4 | Designed NLS peptide. |
| SEQ ID No: 10 to 13 | Designed antiviral peptide. |

BEST MODE FOR CARRYING OUT THE INVENTION

Hereinafter, preferred modes of the present invention will be described. Note that, matters required for carrying out the present invention (for instance, such general items as those related to peptide synthesis, polynucleotide synthesis and preparation of an antiviral agent having a peptide as constituent (antiviral composition)), which are matters other than items in particular referred to herein (for instance, the primary structure and chain length of the antiviral peptide), may be understood as design items for those skilled in the art based on prior art techniques in fields such as organic chemistry, biochemistry, genetic engineering, protein engineering, molecular biology, pharmaceutical sciences, medical science, health science and the like. The present invention can be carried out based on the content disclosed herein and technical common sense in the field. Note that, in the following description, according to circumstances, amino acids are represented by the one letter code (with the proviso that the three-letter code is used in the sequence listing) based on the nomenclature regarding amino acids indicated in the IUPAC-IUB guidelines.

In addition, the entirety of the contents of all the literature cited herein is included herein by reference.

Herein, "non-naturally occurring, artificially synthesized peptide" refers not to a peptide chain that exists stably in nature independently on its own, but to a peptide fragment prepared by artificial chemical synthesis or biosynthesis (that is to say, produced based on genetic engineering), and may exist stably inside a given system (for instance, a drug composition constituting an antiviral agent).

Herein, "amino acid residue" is a term that includes the N-terminal amino acid and the C-terminal amino acid of the peptide chain, except where stated in particular.

Herein, an "amino acid sequence that has been partially modified (modified amino acid sequence)" with respect to a given amino acid sequence refers to an amino acid sequence formed by substitution, deletion and/or addition (insertion) of one or several (for instance nine or fewer, preferably five or fewer, and particularly preferably two or three) amino acid residues, without compromising the antiviral activity of the given amino acid sequence. For instance, sequences generated by so-called conservative substitution (conservative amino acid replacement) comprising one or several (typically, two or three) amino acid residues that have been substituted in a conservative manner (for instance, sequence in which a basic amino acid residue has been replaced by another basic amino acid residue, sequence in which a hydrophobic amino acid residue has been substituted by another hydrophobic amino acid residue), or, sequences comprising one or several (typically, two or three) amino acid residues that have been added (inserted) or deleted in a given amino acid sequence, and the like, are typical examples included in "sequence that has been partially modified (modified amino acid sequence)" referred to herein.

Herein, "antiviral peptide" is a term designating an amino acid polymer having a plurality of peptide bonds and displaying antiviral activity (multiplication inhibition activity) against at least one species of virus, and is not limited by the number of amino acid residues contained in the peptide chain. Oligopeptides with a number of amino acid residues up to on the order of 10, or polypeptides containing more amino acid residues are also included in the antiviral peptide of the present specification.

In other words, the antiviral peptide disclosed herein is a non-naturally occurring, artificially designed peptide, typically, a relatively short polypeptide or oligopeptide having the above-mentioned NLS-related sequence and NES-related sequence as amino acid sequences involved in antiviral expression.

Herein, "NLS" or "nuclear localization sequence" designates all amino acid sequences already known as nuclear transport (nuclear localization) sequence and disclosed as NLS in a variety of journals and other media, and is not limited to a specific amino acid sequence except when mentioned in particular. NLS is known as a portion (domain) of amino acid sequence that is rich in basic amino acid residues.

Conventionally, any native NLS discovered in various living organisms and viruses can be selected and this amino acid sequence be used as NLS-related sequence to design the antiviral peptide of the present invention. Note that examples of native NLS that may be used to design the antiviral peptide of the present invention are shown in SEQ ID No:14 to SEQ ID No:94 (though not limited to these). Among the native NLS's, adoption of a virus-derived NLS is desirable. When adopting a native NLS for which one unit is four amino acid residues or fewer, designing the amino acid sequence to have overall five amino acid residues or more by combining with an identical or a different NLS is desirable. That is to say, designing an NLS-related sequence containing two units or more (typically, two units, three units or four units) NLS's for which one unit is four amino acid residues or fewer is adequate. For instance, if RKRR (SEQ ID No:40) is selected as NLS, a sequence composed of eight amino acid residues in which two units of this sequence has been linked in tandem (RKRRRKRR) can serve as NLS-related sequence.

Although no particular limitation is intended, as typical examples of virus-derived NLS used to prepare an antiviral agent, HIV REV protein-derived RQARRNRRRRVR (SEQ ID No:1), HIV TAT protein-derived RKKRRQRRR (SEQ ID No:2) and SV40 (Simian virus 40)-derived PKKKRKV (SEQ ID No:3) may be cited. In addition, the sequence RKKKRKV shown in SEQ ID No:4 is a desirable example of NLS modified sequence comprising a substitution by an arginine residue of the N-terminal proline residue in NLS from SEQ ID No:3. In addition, the sequence YGRKKRRQRRR shown in SEQ ID No:5 is the HIV TAT protein and includes the NLS from SEQ ID No:2.

Herein, "NES" or "nuclear export signal sequence" designates all amino acid sequences already known as nuclear export signal sequence and disclosed as NES in a variety of journals and other media, and is not limited to a specific amino acid sequence except when mentioned in particular. NES is known as a highly hydrophobic portion (domain) of amino acid sequence that is rich in leucine residues.

Conventionally, any native NES discovered in various living organisms and viruses can be selected and this sequence used untouched as NES-related sequence to design the antiviral peptide of the present invention.

Although no particular limitation is intended, as typical examples of NES used to prepare an antiviral agent, HIV-derived LPPLERLTLD (SEQ ID No:6), mouse PKI (protein kinase inhibitor)-derived LALKLAGLDI (SEQ ID No:7), HIV-derived LPPDLRLTLD (SEQ ID No:8) and HTLV-1 derived LSAQLYSSLSLD (SEQ ID No:9) may be cited.

A peptide having 50% or more of the total number of amino acid residues constituting the peptide chain constituted by NLS-related sequence and NES-related sequence is preferred. Here, one unit (repeat) with regard to NLS-related sequence or NES-related sequence designates one sequence portion (region or motif) constituting the NLS-related sequence or NES-related sequence. Consequently, when two units of NLS-related sequence or NES-related sequence are contained in a peptide chain, it means that two sequences, regardless of whether they are identical or different, identified independently from one another as NLS-related sequences or NES-related sequences are present in the peptide chain. For instance, in the case of a peptide chain in which two amino acid sequences indicated in any from SEQ ID No:1 to 5 are placed in tandem, the peptide has two units of NLS-related sequence. Similarly, for instance, in the case of a peptide chain in which two amino acid sequences indicated in any from SEQ ID No:6 to 9 are placed in tandem, the peptide has two units of NES-related sequence.

A peptide composed of a short peptide chain constituted by one unit of NLS-related sequence and NES-related sequence is a typical example of the antiviral peptide disclosed herein, and is desirable as antiviral peptide serving as main component of an antiviral agent (antiviral composition) (refer to examples described below). While the sequence order of the NLS-related sequence and NES-related sequence is not limited in particular, it is desirable to position the NLS-related sequence on the N-terminal side of the peptide chain, and to position the NES-related sequence on the C-terminal side thereof. In this case, an embodiment in which the C-terminal amino acid of one of the adjacent antivirus-associated sequences (for instance, NLS-related sequence) and the N-terminal amino acid of the other antivirus-associated sequence (for instance, NES-related sequence) are directly bonded is desirable (refer to examples described below). Alternatively, one to several suitable amino acid residues (for instance one to several glycine residues) may be intercalated as a linker between the adjacent NLS-related sequence and NES-related sequence.

While the proportion occupied by NLS-related sequence and NES-related sequence with respect to the overall amino acid sequence (that is to say, the number percentage occupied by the number of amino acid residues constituting the antivirus-associated sequence portion of the total number of amino acid residues constituting the peptide chain) is not limited in particular as long as it is 50% or greater, 70% or greater is more desirable, and 80% or greater is particularly desirable. A peptide in which substantially the entirety (for instance, 90% or greater) of the peptide chain is constituted by NLS-related sequence and NES-related sequence is desirable.

Note that, as the antiviral peptide of the present invention, those in which the entirety of amino acid residues are L-amino acids are desirable; however, as long as the antiviral activity is not lost, those in which a portion or the entirety of the amino acid residues has been substituted by a D-amino acid are also adequate.

The chain length (that is to say the total number of amino acid residues) of the antiviral peptide disclosed herein is not limited in particular as it may differ according to the length of the NLS-related sequence and/or NES-related sequence, a total number of amino acid residue of 100 or fewer (typically, 50 or fewer) being adequate, and in particular, on the order of 30 or fewer is desirable. For instance, with those constituted by on the order of 20 to 30 amino acid residues, high antiviral activity may be obtained while at the same time they are readily synthesized, making their use convenient.

Note that, regarding the conformation of a peptide (tertiary structure), while there is no particular limitation as long as antiviral activity is exerted under the utilization environment, those in linear form or helix form are preferred from the point of view that they are less immunogenic (antigenic). Constituting an epitope is difficult for peptides in such forms. From such points of view, those that are linear and have comparatively low molecular weights (typically, a number of amino acid residues of on the order of 30 or fewer (in particular, on the order of 20 to 30)) are desirable as antiviral peptides for application in an antiviral agent.

Note that, for NLS-related sequence and NES-related sequence, while native NLS and NES may be adopted as-is, an antiviral peptide (peptide chain) can also be designed readily by adopting a sequence obtained by modifying either native amino acid sequence, for instance, NLS-related sequence (modified sequence) and/or NES-related sequence (modified sequence) constituted by substituting, deleting and/or adding one or several (preferably about 2 to 5) amino acid residues.

For instance, either native amino acid sequence (for instance NLS in SEQ ID No:3) can be taken as a base for the creation of an modified sequence, from where the sequence can be modified onward with adequate antiviral activity tests (for instance, a variety of multiplication suppression tests carried out in vitro) as indicators. Substitution, deletion or addition (insertion) of amino acid residue can be cited as alteration means. That is to say, based on a native amino acid sequence, substitution, deletion or addition (insertion) of one to several amino acid residues is carried out arbitrarily, peptides containing these modified sequences are prepared, and given antiviral activity tests (refer to examples described below) are carried out. In this way, whether or not the modified sequences are desirable for designing an antiviral peptide can be discriminated readily.

For instance, from the point of view of decreasing manufacturing cost or helping chemical synthesis, deletion of amino acid residue is desirable. In terms of increasing structure stability, addition of amino acid residue is desirable. In addition, from the point of view of increasing antiviral activity, substitution of amino acid residue is desirable.

To the extent that antiviral property is not lost, the antiviral peptide used may partially contain a sequence that may not be contained in an anti virus-associated sequence. While there is no particular limitation, a sequence that may maintain the three-dimensional shape (typically linear chain shape) of the antivirus-associated sequence portion in a peptide chain is desirable as such partial sequence.

In addition, the antiviral peptide used preferably has at least one amino acid residue that is amidated. The structure stability (for instance, resistance to protease) of the antiviral peptide may be improved by amidation at the carboxyl group of an amino acid residue (typically, the C-terminal amino acid residue of a peptide chain).

The antiviral peptide disclosed herein can be prepared readily according to a general chemical synthesis method. For instance, either prior art well known solid phase synthesis method or liquid phase synthesis method may be adopted. Solid phase synthesis methods that apply Boc (t-butyloxycarbonyl) or Fmoc (9-fluorenylmethoxycarbonyl) as amino-protecting group are desirable. As the antiviral peptide disclosed herein can be synthesized a peptide chain having the desired amino acid sequence and modified (C-terminal amidation or the like) moiety by the solid phase synthesis method using a commercial peptide synthesizer (for instance, available from PerSeptive Biosystems, Applied Biosystems and the like).

Alternatively, the antiviral peptide may be biosynthesized based on a genetic engineering method. This approach is desirable when preparing a polypeptide with a comparatively long peptide chain. That is to say, a DNA with the nucleotidic sequence (including the ATG start codon) coding for the amino acid sequence of the desired antiviral peptide is synthesized. Then, a recombinant vector having a gene construct for expression use composed of a variety of regulatory elements (including a promoter, a ribosome binding site, a terminator, an enhancer and a variety of cis elements regulating the expression level) to express this DNA and the amino acid sequence inside a host cell is constructed according to the host cell.

This recombinant vector is introduced into a given host cell (for instance, yeast, insect cell, plant cell or animal (mammalian) cell) by a general technique, and the host cell; or tissue or individual containing the cell is cultured under given conditions. This allows the target polypeptide to be expressed and produced in a cell. Then, the polypeptide is isolated from the host cell (from within the culture medium if secreted) and purified, allowing the target antiviral peptide to be obtained.

Note that for methods for constructing a recombinant vector, methods for introducing the constructed recombinant vector into a host cell, and the like, adopting prior art methods carried out in the field as-is sufficient, and since such methods per se do not characterize the present invention in particular, detailed description will be omitted.

For instance, fusion protein expression system can be used for efficient, large quantity production in a host cell. That is to say, the gene (DNA) coding for the amino acid sequence of the target antiviral peptide is chemically synthesized, and the synthesized gene is introduced at a desirable site of an adequate fusion protein expression vector (for instance, GST (Glutathione S-transferase) fusion protein expression vectors such as pET series provided by Novagen and pGEX series provided by Amersham Bioscience). Then, a host cell (typically, *Escherichia coli*) is transformed with the vector. The obtained transformant is cultured to prepare the target fusion protein. Next, the protein is extracted and purified. The obtained purified fusion protein is cleaved with a given enzyme (protease), and the released target peptide fragment (designed antiviral peptide) is recovered by a method such as affinity chromatography. Using such conventionally known fusion protein expression system (for instance, GST/H is system provided by Amersham Bioscience may be used) allows the antiviral peptide of the present invention to be prepared.

Alternatively, the target polypeptide can be synthesized in vitro by constructing a template DNA for cell-free protein synthesis system (that is to say, a synthetic gene fragment containing a nucleotidic sequence coding for the amino acid sequence of the antiviral peptide), using a variety of compounds necessary for peptide synthesis (ATP, RNA polymerase, amino acids and the like) and adopting a so-called cell-free protein synthesis system. Regarding cell-free protein synthesis system, for instance article by Shimizu et al. (Shimizu et al., Nature Biotechnology, 19, 751-755 (2001)) and article by Madin et al. (Madin et al., Proc. Natl. Acad. Sci. USA, 97 (2), 559-564 (2000)) can be referenced. The entirety of the contents of these articles is incorporated herein by reference. Based on the techniques described in these articles, at the time of this application, already a number of companies are carrying out contracted production of polypeptides, and in addition, kits for cell-free protein synthesis (for instance, PROTEIOS (registered trademark) Wheat germ cell-free protein synthesis kit available from the Toyobo of Japan) are commercialized.

Consequently, determining once the amino acid sequence to be used and designing the peptide chain as described above is all that is needed to allow the target antiviral peptide to be synthesized and produced readily by a cell-free protein synthesis system according to this amino acid sequence. For instance, the antiviral peptide of the present invention can be produced readily based on PURESYSTEM (registered trademark) from Post Genome Institute of Japan.

In addition, the present invention provides a non-naturally occurring, artificially designed polynucleotide containing a nucleotidic sequence coding for any antiviral peptide disclosed herein and/or a nucleotidic sequence complementary to this sequence (for instance, polynucleotides substantially constituted by these sequences).

Herein "polynucleotide" is a term designating a polymer composed of several nucleotides linked by phosphodiester bonds (nucleic acid), and is not limited by the number of nucleotides. DNA fragments and RNA fragments with a variety of lengths are included in the polynucleotides of the present specification. In addition, "non-naturally occurring, artificially designed polynucleotide" means a polynucleotide which nucleotide chain (full length) does not exist alone in nature, and has been artificially synthesized by chemical synthesis or biosynthesis (that is to say, production based on genetic engineering).

For instance, polynucleotides containing nucleotide sequences coding for any amino acid sequence of SEQ ID No:10 to SEQ ID No:13 (or modified sequences obtained by partial alteration of the sequences) (for instance, polynucleotides substantially constructed by these sequences) and/or nucleotide sequences complementary to the sequences may be cited as preferred polynucleotides. Note that, there is no particular limitation on the selection of codon defining each amino acid, and a selection while taking into consideration the usage frequency in the usable host cell is sufficient.

A single stranded or double stranded polynucleotide containing the nucleotide sequence coding for the antiviral peptide disclosed herein and/or the nucleotide sequence complementary to the sequence can be prepared (synthesized) readily by conventionally known methods. That is to say, by selecting the codon corresponding to each amino acid residue constituting the designed amino acid sequence, nucleotide sequence corresponding to the amino acid sequence of the antiviral peptide is readily determined and provided. Then, if the nucleotide sequence is determined once, using a DNA synthesizer or the like, a polynucleotide (single strand) corresponding to the desired nucleotide sequence can be readily obtained. Furthermore, using the obtained single strand DNA as a template and adopting a variety of enzymatic synthesis means (typically, PCR), the target double strand DNA can be obtained.

The polynucleotide provided by the present invention may be in DNA form or may be in RNA (mRNA or the like) form. The DNA may be provided in double strand or single strand. If provided in single strand, it may be a coding strand (sense strand) or it may be a sequence complementary thereto, a non-coding strand (antisense strand).

The polynucleotide provided by the present invention can be used as material for constructing a recombinant gene (expression cassette) for antiviral peptide production in a variety of host cells or in a cell-free protein synthesis system, as described above.

According to the present invention, a non-naturally occurring, artificially designed polynucleotide is provided, containing a nucleotide sequence coding for an antiviral peptide with an novel amino acid sequence containing a sequence produced by altering a native NLS and/or an modified sequence produced by altering a native NES, and/or a nucleotide sequence complementary to the sequence.

The antiviral peptide of the present invention has a high antiviral activity against at least one species of virus. For instance, it may exert a high antiviral activity against double-stranded DNA viruses such as a variety of herpes viruses. In addition, it may exert antiviral activity also against single-stranded RNA viruses such as those belonging to orthomyxoviridae, flaviviridae and retroviridae. The antiviral peptide of the present invention is preferably used in particular for the suppression of influenza virus multiplication.

The antiviral peptide disclosed herein has a comparatively broad antiviral spectrum and is used preferably as main component of an antiviral agent (antiviral composition). For instance, it may be used for purposes such as treatment of viral infection disease, prevention of viral disease such as sexually transmitted disease, mouth washing (gargle) and eye washing.

Note that, the antiviral peptide contained in the antiviral agent may be in salt form, as long as the antiviral activity is not lost. For instance, an acid addition salt of the peptide obtained by addition reaction with an inorganic acid or an organic acid commonly used according to conventional methods can be used. Alternatively, it may be another salt (for instance metal salt) as long as it has antiviral activity.

An antiviral agent used for such purposes may contain, in addition to the antiviral peptide serving as main component, a variety of pharmacologically (pharmaceutically) acceptable carriers (media, carriers and the like). Carriers used generally in peptide medicine as diluent, excipient and the like, are preferred. Although there may be suitable differences according to the form and application of the antiviral agent, typically, water, physiological buffer solution such as physiological saline, a variety of organic solvents may be cited. For instance, it may be an adequately concentrated aqueous solution of alcohol (ethanol or the like), glycerol, or nondrying oil such as olive oil. Or it may be a liposome. In addition, as secondary components that may be included in the antiviral agent, a variety of filler, expander, binder, moisturizer, surfactant, dye, flavor and the like may be cited.

There is no particular limitation on the form of the antiviral agent. For instance, as typical forms of agent for internal use or external use, ointment, solution, suspension, emulsion, aerosol, foam, granule, powder, tablet and capsule may be cited. In addition, for use in injection or the like, it may be a lyophilizate or a granule to be dissolved immediately before use in physiological saline or a suitable buffer solution (for instance PBS) or the like to prepare a drug solution. The carrier contained in the antiviral agent may differ according to the form of the antiviral agent.

Note that the process per se for preparing an agent (composition) in a variety of forms with the antiviral peptide (main component) and a variety of carriers (secondary components) as materials only needs to follow conventionally known methods, and since such formulation methods per se do not characterize the present invention, detailed description will be omitted. As a detailed source of information regarding prescription, for instance, Comprehensive Medicinal Chemistry, Corwin Hansch, Pergamon Press (1990) may be given. The entirety of the content of the literature is incorporated herein by reference.

The antiviral agent (antiviral composition) provided by the present invention can be used with methods and dosages according to the form and purpose thereof.

The antiviral peptide containing the antivirus-associated sequence disclosed herein may maintain high antiviral activity even in systems where present are comparatively high concentration of cations, salts (for instance sodium chloride) or organic compound, such as serum. Consequently, the antiviral agent disclosed herein is used preferably in systems (places) where cation, salts, serum and the like are present. For instance, the antiviral agent (antiviral composition) provided by the present invention can be administered to a patient as a liquid agent by intravascular, intramuscular, subcutaneous, intracutaneous or intraperitoneal injection or enema.

Consequently, one preferred mode of viral multiplication suppression method provided by the present invention is a method whereby a liquid composition containing any antiviral peptide disclosed herein is administered to a patient by intravascular, intramuscular, subcutaneous, intracutaneous or intraperitoneal injection or enema.

Alternatively, those in solid form such as tablet can be administered orally. Consequently, one preferred mode of viral multiplication suppression method provided by the present invention is a method whereby a composition containing any antiviral peptide disclosed herein in solid form, liquid form or gel form is orally administered to a patient.

Alternatively, when using the invention for the purpose of cleaning sanitary ware surfaces, either directly spraying a solution containing comparatively large amounts (for instance 1 to 100 mg/ml) of antiviral peptide on the surface of the target object, or, wiping the surface of the target with a cloth or paper soaked in the solution agent is adequate. These are mere examples, and similar forms and employment methods as conventional peptide antibiotics; or pesticides, quasi drugs and the like, having a peptide as a component, can be applied. Consequently, one preferred mode of viral multiplication suppression method provided by the present invention is a method whereby a composition containing any antiviral peptide disclosed herein (typically, a solution) is applied to a sanitary ware (toilet or the like) or other target objects.

In addition, a polynucleotide coding for the antiviral peptide of the present invention may be used as material to be used in so-called gene therapy. For instance, a gene coding for an antiviral peptide (typically, a DNA segment or an RNA segment) can be integrated into a suitable vector and introduced into a target site, allowing the antiviral peptide according to the present invention to be expressed in an organism (cell) constitutively. Consequently, a polynucleotide coding for the antiviral peptide of the present invention (DNA segment, RNA segment and the like) is useful as drug for preventing or treating a viral infection.

In the field of regenerative medicine, it is important to prevent viral infection during culturing of skin, bone and various organs. The antiviral peptide disclosed herein has extremely low toxicity to mammalian cells and tissues, and may display antiviral action selectively to viruses. Therefore, it is extremely useful as a drug for preventing viral infection of cultured organs or the like. For instance, as shown in the examples described below, adding at a suitable concentration the antiviral peptide of the present invention alone or an antiviral agent (antiviral composition) having the peptide as one of the main components into the culture solution can prevent biological objects such as organs, tissues and cells in culture from being infected by a virus. Consequently, one preferred mode of viral multiplication suppression method provided by the present invention is a method whereby any antiviral peptide disclosed herein is added into a culture solution of organs (organs), tissues or cells as target objects.

In addition, a polynucleotide coding for the antiviral peptide of the present invention can be used as material to be used in gene therapy in cultured cells and cultured tissues. For instance, a gene coding for the antiviral peptide of the present invention (typically, a DNA segment or an RNA segment) can be integrated into a suitable vector and introduced into the target culture tissue, allowing the antiviral peptide according to the present invention to be expressed in a cultured tissue (cell) constitutively or at a desired time period. Consequently, a polynucleotide coding for the antiviral peptide provided by the present invention (DNA segment, RNA segment and the like) is useful as a drug for preventing viral infection of cultured tissue.

Hereinafter, a number of examples pertaining to the present invention will be described; however, it is not intended to limit the present invention to those examples.

EXAMPLE 1

Peptide Synthesis

A total of eight species of peptide (Samples 1 to 4, Comparative Samples 1 to 4) were prepared using the peptide synthesizer mentioned below. Table 1 lists the amino acid sequences of these synthesized peptides.

TABLE 1

| Sample No. | amino acid sequence | SEQ ID No. | total number of amino acid residues |
|---|---|---|---|
| Sample 1 | RQARRNRRRRWR LPPLERLTLD-$CONH_2$ | 10 | 22 |
| Sample 2 | LPPLERLTLD RQARRNRRRRWR-$CONH_2$ | 11 | 22 |
| Sample 3 | YGRKKRRQRRR LPPLERLTLD-$CONH_2$ | 12 | 21 |
| Sample 4 | RKKKRKV LALKAGLDI-$CONH_2$ | 13 | 16 |
| Comparative Sample 1 | RQARRNRRRRWR-$CONH_2$ | 1 | 12 |
| Comparative Sample 2 | LPPLERLTLD-$CONH_2$ | 6 | 10 |
| Comparative Sample 3 | YGRKKRRQRRR-$CONH_2$ | 5 | 11 |
| Comparative Sample 4 | RKKKRKV-$CONH_2$ | 4 | 7 |

As shown in Table 1, Samples 1 to 4 all have one unit of NLS-related sequence and one unit of NES-related sequence adjacent to one another.

That is to say, the peptide of Sample 1 (SEQ ID No:10) has the HIV REV protein-derived RQARRNRRRRWR (SEQ ID No:1) as the NLS-related sequence on the N-terminal side of the peptide chain, and on the C-terminal side thereof, has the HIV-derived LPPLERLTLD (SEQ ID No:6) as the NES-related sequence.

Conversely to Sample 1, the peptide of Sample 2 (SEQ ID No:11) has the NES-related sequence LPPLERLTLD (SEQ ID No:6) on the N-terminal side of the peptide chain, and on the C-terminal side thereof, has RQARRNRRRRWR (SEQ ID No:1) as the NLS-related sequence.

The peptide of Sample 3 (SEQ ID No:12) has HIV TAT protein YGRKKRRQRRR (SEQ ID No:5) as the NLS-related sequence on the N-terminal side of the peptide chain, and on the C-terminal side thereof, has the HIV-derived LPPLERLTLD (SEQ ID No:6) as the NES-related sequence.

The peptide of Sample 4 (SEQ ID No:13) has RKKKRKV (SEQ ID No:4), which is a modified sequence from the SV40-derived NLS (SEQ ID No:3), on the N-terminal side of the peptide chain as the NLS-related sequence, and on the C-terminal side thereof, has a modified sequence from the mouse PKI-derived LALKLAGLDI (SEQ ID No:7), from which one leucine residue has been deleted, as the NES-related sequence.

Meanwhile, the peptide of Comparative Sample 1 is composed of the NLS-related sequence RQARRNRRRRWR (SEQ ID No:1) only. The peptide of Comparative Sample 2 is composed of the NES-related sequence LPPLERLTLD (SEQ ID No:6) only. The peptide of Comparative Sample 3 is composed of the NLS-related sequence YGRKKRRQRRR (SEQ ID No:5) only. The peptide of Comparative Sample 4 is composed of the NLS-related sequence RKKKRKV (SEQ ID No:4) only.

Note that all the samples have the carboxyl group (—COOH) of the C-terminal amino acid amidated (—CONH$_2$).

Each peptide described above was synthesized using a commercial peptide synthesizer (PEPTIDE SYNTHESIZER 9050, product of PerSeptive Biosystems) by the solid phase synthesis method (Fmoc method). HATU (product of Applied Biosystems) was used as condensation agent, and the resin and amino acids used in the solid phase synthesis method were purchased from NOVA biochem. When amidating the C-terminus of the amino acid sequence, "Rink Amide resin (100 to 200 mesh)" was used as a solid phase carrier.

Next, deprotection reaction and condensation reaction were repeated according to the synthesis program of the above-mentioned peptide synthesizer to extend the peptide chain from the Fmoc-amino acid bonded to the resin and obtain the synthetic peptide with the target chain length. In particular, the operation of cleaving and eliminating Fmoc, which is an amino protecting group for amino acid, with 20% piperidine/dimethyl formamide (DMF) (peptide synthesis grade, product of Kanto Kagaku), washing with DMF, reacting with 4 eq each of Fmoc-amino acid (—OH) and washing with DMF was repeated. Then, after the peptide chain elongation reaction has ended completely, the Fmoc group was cleaved with 20% piperidine/DMF and the above resin was washed in the DMF and methanol order.

After the solid phase synthesis, the synthesized peptide chain together with resin was transferred to a centrifugation tube, 1.8 mL of ethane diol, 0.6 mL of m-cresol, 3.6 mL of thioanisole and 24 mL of trifluoroacetic acid were added, and the mixture was stirred at room temperature for two hours. Thereafter, the resin that had been bonded to the peptide chain was filtered and eliminated.

Cold ethanol was added to the filtrate, and peptide precipitate was obtained by cooling with ice-cold water. Thereafter, supernatant was eliminated by centrifugal separation (at 2500 rpm for 5 minutes). Cold diethyl ether was added newly to the precipitate and thoroughly stirred, then centrifugal separation was carried out under the same conditions as above. This step of stirring and centrifugal separation was carried out for a total of three times.

The obtained peptide precipitate was dried under vacuum, and purification was carried out using high performance liquid chromatograph (Waters 600: product by Waters).

In particular, a pre-column (available from Japan Waters, Guard-Pak Delta-pak C18 A300) and a C18 reverse phase column (available from Japan Waters, XTerra (registered trade mark) column, MS C18, 5 µm, 4.6×150 mm) were used, and a mixed solution of 0.1% trifluoroacetic acid aqueous solution and 0.1% trifluoroacetic acid acetonitrile solution was used for elution solution. That is to say, separation and purification were carried out over 30 to 40 minutes using the above column at a flow rate of 1.5 mL/minute while increasing the proportion of the above trifluoroacetic acid acetonitrile solution contained in the elution solution over time (setting a concentration gradient from 10% to 80% in volume ratio). Note that the peptide eluted from the reverse phased column was detected using an ultraviolet light detector (490E Detector: product by Waters) at a wavelength of 220 nm, and is shown as a peak on the recording chart.

In addition, the molecular weight of each eluted peptide was determined using Voyager DE RP (trade mark) by PerSeptive Biosystems, based on MALDI-TOF/MS (Matrix-Assisted Laser Desorption Time of Flight Mass Spectrometry). As a result, it was determined that the target peptides were synthesized and purified.

EXAMPLE 2

Antiviral Activity of Synthetic Peptide (1)

The antiviral activity (viral multiplication suppression effect) was examined for each sample antiviral peptide and each comparative sample peptide. In the present example, HVT (turkey herpes virus) was used as the target virus, and the titer was measured based on the plaque assay method.

That is to say, chicken embryo fibroblast (CEF) cells prepared from SPF (specific pathogen-free) embryonated hen's egg (purchased from Nisseiken Co., LTD) were monolayer-cultured at 37° C. using Leibowitz-McCoy 5A (1:1) mixed culture medium (LM medium). The culture was peeled from the culture dish by trypsin digestion and transferred to a 50 mL centrifugation tube. After centrifugal separation, the supernatant was discarded and the culture was suspended with LM medium.

HVT (FC-126 strain used as vaccine), which virus titer was measured beforehand, was diluted with this cell suspension to as to have 100 plaque forming units (PFU) or 400 PFU per 2 mL. This dilute solution was dispensed in each well of a 6-well plate, 2 mL in each. Then, the test peptides (Samples 1 to 4, Comparative Samples 1 to 4) were diluted with PBS to be at 2.1 mM, 1050 μM and 210 μM, and added to each well, 0.1 mL in each. The final concentration of each well after addition was respectively 100 μM, 50 μM and 10 μM. A well to which 0.11 mL of PBS not containing peptide was added was prepared as a reference.

In addition, as a control group for evaluating the cytotoxicity of the test peptide, wells were prepared in which 2 mL each of a suspension of CEF cells alone not containing virus at all were distributed, and peptides at each concentration were added, 0.1 mL in each.

Thereafter, the above 6-well plate was placed in a $CO_2$ incubator (5% $CO_2$), cultured at 37° C. for six days, and the number and size of HVT plaques that appeared were observed. Here, comparing with wells with no peptide added, when a drop in the number of plaques or a reduction in the size of plaques was not observed even when a peptide was added, the viral multiplication suppression effect of this peptide was determined to be none. On the other hand, a test peptide for which a well with smaller plaque number or plaque size was present, the titer of each well was measured, and the viral multiplication suppression effect (antiviral activity) was quantified by comparing with the quantity of virus with no peptide added.

For the method for measuring the HVT virus titer, cells in each well were recovered by trypsin digestion, serially diluted, mixed again with CEF cells, dispensed in a 6-well plate and cultured at 37° C., and the number of plaques appeared after six days were counted. The relative ratio of virus titer at each peptide concentration was determined with the virus titer (PFU/mL) of the well with no peptide added being 1. That is to say, the viral multiplication suppression effect of each test peptide can be compared using the value of this relative ratio (Ratio).

The result is shown in Table 2.

In addition, no cytotoxicity was observed in any sample, indicating the usefulness of the antiviral agent provided by the present invention.

EXAMPLE 3

Antiviral Activity of Synthetic Peptide (2)

Antiviral activity (viral multiplication suppression effect) was examined for Sample 1 and Sample 4, with another virus as the target.

In the present example, MDV (Marek's disease virus), which is a species of herpes virus that infect birds, was used as the target virus, and the titer (infectivity titer) was measured based on the $TCID_{50}$ (50% Tissue Culture Infections Dose) method.

That is to say, chicken embryo fibroblast (CEF) cells prepared from SPF embryonated hen's egg (purchased from Nisseiken Co., LTD) were monolayer-cultured at 37° C. using Leibowitz-McCoy 5A (1:1) mixed culture medium (LM medium). The culture was peeled from the culture dish by trypsin digestion and transferred to a 50-mL centrifugation tube. After centrifugal separation, the supernatant was discarded and the culture was suspended with LM medium.

MDV type 1 (MDV Serotype 1) Md5 strain, which virus titer was measured beforehand, was diluted with this cell suspension to as to have $2\times10^2$ $TCID_{50}$ per 2 mL. This dilute solution was dispensed in each well of a 6-well plate, 2 mL in each. Then, the test peptides (Samples 1 to 4, Comparative Samples 1 to 4) were diluted with PBS to be at 2.1 mM and 1050 μM, and added to each well, 0.1 mL in each. The final concentration of each well after addition was respectively 100 μM and 50 μM. A well to which 0.1 mL of PBS not containing peptide was added was prepared as a reference.

In addition, as a control group for evaluating the cytotoxicity of the test peptide, wells were prepared in which 2 mL

TABLE 2

| | Concentration of Peptide | | | | | | | |
|---|---|---|---|---|---|---|---|---|
| | 0 μM | | 10 μM | | 50 μM | | 100 μM | |
| Sample No. | Titer | Ratio | Titer | Ratio | Titer | Ratio | Titer | Ratio |
| Sample 1 | $1.04 \times 10^5$ | 1.0 | $7.8 \times 10^4$ | 0.75 | $2.6 \times 10^4$ | 0.25 | $1.4 \times 10^4$ | 0.13 |
| Sample 2 | $8.8 \times 10^4$ | 1.0 | $8.0 \times 10^4$ | 0.91 | $5.2 \times 10^4$ | 0.59 | $5.0 \times 10^4$ | 0.57 |
| Sample 3 | $8.8 \times 10^4$ | 1.0 | $7.3 \times 10^4$ | 0.83 | $5.2 \times 10^4$ | 0.59 | $3.3 \times 10^4$ | 0.38 |
| Sample 4 | $1.9 \times 10^4$ | 1.0 | $1.8 \times 10^4$ | 0.95 | $9.0 \times 10^3$ | 0.47 | $4.5 \times 10^3$ | 0.24 |
| Comparative Sample 1 | | | no viral multiplication suppression effect | | | | | |
| Comparative Sample 2 | | | no viral multiplication suppression effect | | | | | |
| Comparative Sample 3 | | | no viral multiplication suppression effect | | | | | |
| Comparative Sample 4 | | | no viral multiplication suppression effect | | | | | |

Titer: PFU/mL

As is apparent from Table 2, all of each sample peptide having an NLS-related sequence and an NES-related sequence showed satisfactory antiviral activity (viral multiplication suppression effect). On the other hand, for each comparative sample peptide composed of the NLS-related sequence only or the NES-related sequence only, no antiviral activity (viral multiplication suppression effect) was observed at all.

each of a suspension of CEF cells alone not containing virus at all were distributed, and peptides at each concentration were added, 0.1 mL in each.

Thereafter, the above 6-well plate was placed in a $CO_2$ incubator (5% $CO_2$), and cultured at 37° C. for four days. Then, the titer of MDV virus multiplied in each well was measured as indicated below.

That is to say, cells in each well were recovered by trypsin digestion and serially diluted again with a CEF cell suspension, each dilute solution was respectively dispensed over five wells of a 24-well plate and cultured at 37° C. Four days later, whether or not a CPE (cytopathic effect) occurred in the well was examined. Infectivity titer ($TCID_{50}$) was calculated from this result by the Reed-Muench method (Reed and Muench method), which is a conventional method. The result is shown in Table 3.

TABLE 3

| Sample No. | Concentration of Peptide | | | | | |
|---|---|---|---|---|---|---|
| | 0 μM | | 50 μM | | 100 μM | |
| | Titer | Ratio | Titer | Ratio | Titer | Ratio |
| Sample 1 | $6.76 \times 10^6$ | 1.0 | $2.40 \times 10^6$ | 0.36 | $6.76 \times 10^5$ | 0.1 |
| Sample 4 | $6.76 \times 10^6$ | 1.0 | $4.27 \times 10^6$ | 0.63 | $3.16 \times 10^6$ | 0.47 |

Titer: $TCID_{50}$

As is apparent from Table 3, both Sample 1 and Sample 4 displayed satisfactory antiviral activity (viral multiplication suppression effect) against MDV. From this result, it was confirmed that the antiviral peptide disclosed herein may exert antiviral activity against several types of viruses. In addition, no cytotoxicity was observed in any sample.

EXAMPLE 4

Antiviral Activity of Synthetic Peptide (3)

Antiviral activity (viral multiplication suppression effect) against influenza virus, which infects humans, was examined for a portion of the samples (above-mentioned Sample 3). In the present example, the "A/New Calcdonia/20/99 (H1N1)" strain, which is an A-Soviet type (H1N1) influenza virus strain, was used as the target virus, MDCK (Madrin Darby Canine Kidney) cell, which is a canine kidney-derived established cell line, was used as infection cell, and multiplication inhibition assay (plaque assay) was carried out similarly to below.

That is to say, a cell suspension containing MDCK cells added to an Eagle MEM medium (containing kanamycin and sodium bicarbonate) containing 10% FBS, was added to each well of a 6-well plate, 3 mL in each. This plate was placed in a $CO_2$ incubator (5% $CO_2$) and cultured at 37° C. for three days.

The culture supernatant was removed from wells where a full sheet (monolayer) composed of MDCK cells was formed by the above culture. 2 mL of PBS was added to the wells and the wells were washed. This washing was repeated twice. Next, a viral solution prepared with MEM medium (no FBS added, containing 0.02% dextran and 1 μg/mL trypsin) so as to have $10^4$ PFU/mL was used for inoculation at 0.1 mL per well, and culture was incubated in the presence of 5% $CO_2$, at 34° C. for one hour, to adsorb the virus to the cells. After the incubation, was added 2 mL of MEM medium (no FBS added, containing 0.02% dextran and 1 μg/mL trypsin) containing the test peptide at a given concentration so as to have 50 μM and 10 μM final concentrations of peptide in each well after addition. Note that a well was prepared as a control plot (control), in which 2 mL of the above-mentioned MEM medium not containing peptide was added. In addition, as the control group for evaluating the cytotoxicity of the test peptide, 2 mL of MEM medium (no FBS added, containing 0.02% dextran and 1 μg/mL trypsin) containing the test peptide at a given concentration was added each to wells (with full sheet formed) containing MDCK cells to which the above-mentioned viral solution was not added (that is to say, not containing virus). Then incubation was carried out in the presence of 5% $CO_2$ at 34° C. for 48 hours.

After 48 hours of incubation, on the condition that cell degeneration was observed in the above control (no test peptide added), the culture supernatant was recovered from each test well and the infectivity titer of the virus contained in the supernatant was determined by plaque assay.

In particular, a cell suspension containing MDCK cells in an Eagle MEM medium (containing kanamycin and sodium bicarbonate) containing 10% FBS was added to each well of a 6-well plate, 3 mL in each, and incubated in the presence 5% $CO_2$, at 37° C. for three days. The culture supernatant was removed from wells where a full sheet (monolayer) composed of MDCK cells was formed by the culture, and the wells were washed twice with 2 mL of PBS. After washing, the above recovered culture supernatant was diluted stepwise with PBS to prepare a series of dilute solutions (sample group for assay test), each dilute solution was used for inoculation at 1 mL per well, and incubation was carried out in the presence of 5% $CO_2$, at 34° C. for one hour. Thereafter, 3 mL of MEM agar medium (no FBS added, containing 0.02% dextran and 1 μg/mL trypsin) was added (overlaid) to the wells, and left at room temperature until the medium solidified. Once solidified, the plate was turned over, and incubation was carried out in this state in the presence of 5% $CO_2$, at 34° C. for three days.

Next, PBS containing 3.7% formalin was added at 2 mL per well, and cells in the wells were fixed by leaving at least for one hour. Thereafter, agar was removed with running water, and cells in the wells were stained by adding 2 mL of a 0.03% methylene blue solution and leaving for at least one hour. After staining, the wells were rinsed, [the plate was] turned over and [the cells were] dried naturally. After leaving overnight in this way, the number of plaques in the wells was counted to calculate the PFU. The above plaque assay was carried out twice in total. The result is shown in Table 4.

TABLE 4

| Sample No. | Concentration of Peptide | Infectivity Titer (PFU/mL) | |
|---|---|---|---|
| | | Trial 1 | Trial 2 |
| Control | 0 μM | $2.1 \times 10^9$ | $2.1 \times 10^9$ |
| Sample 3 | 50 μM | $6.8 \times 10^8$ | $7.9 \times 10^8$ |
| Sample 3 | 100 μM | $6.1 \times 10^8$ | $3.2 \times 10^8$ |

As shown in Table 4, multiplication of influenza virus could be suppressed by the addition of Sample 3. In addition, it was determined that the higher the peptide concentration is, the lower the value of infectivity titer (PFU) becomes. This demonstrates that a peptide having an NLS-related sequence and an NES-related sequence has satisfactory anti influenza virus activity. In addition, similarly to the above examples, no cytotoxicity was observed for the sample peptide.

EXAMPLE 5

Preparation of Granules

After mixing 50 mg of peptide from Sample 1, 50 mg of crystalline cellulose and 400 mg of lactose, 1 mL of mixed solution of ethanol and water was added and the mixture was kneaded. This kneaded mix was granulated according to conventional method to obtain a granule (granular antiviral composition) having antiviral peptide as main component.

Thus, examples of the present invention were described in detail; however these are mere examples and do not limit the claims. The techniques recited in the claims include examples illustrated above, which have been altered or modified in various ways.

For instance, in the present example, as NES-related sequence, those shown in SEQ ID No:6 and SEQ ID No:7 have been adopted; however, other already-known NES (for instance, those indicated in SEQ ID No:8 or SEQ ID No:9) or modified sequences thereof may also be adopted.

What is claimed is:

1. A method for suppressing multiplication of a virus, comprising:

administering a peptide to a subject in need thereof, wherein said peptide contains a first segment and a second segment;

wherein said first segment is composed of at least five contiguous amino acid residues of a nuclear localization sequence (NLS), or a modified amino acid sequence of the NLS in which a single basic amino acid residue has been replaced with another basic amino acid residue, or a single hydrophobic amino acid residue has been replaced with another hydrophobic amino acid residue, or a modified amino acid sequence of the NLS in which two or three basic amino acid residues have each been replaced with another basic amino acid residue, or in which two or three hydrophobic amino acid residues have each been replaced with another hydrophobic amino acid residue, and wherein said second segment is composed of at least five contiguous amino acid residues of a nuclear export signal sequence (NES), or a modified amino acid sequence of the NES in which a single basic amino acid residue has been replaced with another basic amino acid residue, or a single hydrophobic amino acid residue has been replaced with another hydrophobic amino acid residue, or a modified amino acid sequence of the NES in which two or three basic amino acid residues have each been replaced with another basic amino acid residue, or in which two or three hydrophobic amino acid residues have each been replaced with another hydrophobic amino acid residue.

2. The method according to claim 1, wherein the first segment and second segment are positioned contiguously with respect to each other.

3. The method according to claim 2, wherein the peptide is constituted with a total number of 30 or fewer amino acid residues.

4. The method according to claim 1, wherein the virus is influenza virus.

* * * * *

SEQUENCE LISTING

<160> NUMBER OF SEQ ID NOS: 94

<210> SEQ ID NO 1
<211> LENGTH: 12
<212> TYPE: PRT
<213> ORGANISM: Human immunodeficiency virus

<400> SEQUENCE: 1

Arg Gln Ala Arg Arg Asn Arg Arg Arg Arg Trp Arg
1               5                   10

<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
1               5

<210> SEQ ID NO 4
<211> LENGTH: 7
<212> TYPE: PRT
<213> ORGANISM: Artificial Sequence
<220> FEATURE:
<223> OTHER INFORMATION: Designed NLS peptide

<400> SEQUENCE: 4

Arg Lys Lys Lys Arg Lys Val
1               5

<210> SEQ ID NO 5
<211> LENGTH: 11
<212> TYPE: PRT
<213> ORGANISM: Human immunodeficiency virus

<400> SEQUENCE: 5

Tyr Gly Arg Lys Lys Arg Arg Gln Arg Arg Arg
1               5                   10

<210> SEQ ID NO 6
<211> LENGTH: 10
<212> TYPE: PRT
<213> ORGANISM: Human immunodeficiency virus

```
<400> SEQUENCE: 6

Leu Pro Pro Leu Glu Arg Leu Thr Leu Asp
1               5                   10

<210> SEQ ID NO 7
<211> LENGTH: 10
<212> TYPE: PRT
<213> ORGANISM: Mus musculus

<400> SEQUENCE: 7

Leu Ala Leu Lys Leu Ala Gly Leu Asp Ile
1               5                   10

<210> SEQ ID NO 8
<211> LENGTH: 10
<212> TYPE: PRT
<213> ORGANISM: Human immunodeficiency virus

<400> SEQUENCE: 8

Leu Pro Pro Asp Leu Arg Leu Thr Leu Asp
1               5                   10

<210> SEQ ID NO 9
<211> LENGTH: 12
<212> TYPE: PRT
<213> ORGANISM: Human T-cell lymphotropic virus type 1

<400> SEQUENCE: 9

Leu Ser Ala Gln Leu Tyr Ser Ser Leu Ser Leu Asp
1               5                   10

<210> SEQ ID NO 10
<211> LENGTH: 22
<212> TYPE: PRT
<213> ORGANISM: Artificial sequence
<220> FEATURE:
<223> OTHER INFORMATION: Designed antiviral peptide

<400> SEQUENCE: 10

Arg Gln Ala Arg Arg Asn Arg Arg Arg Trp Arg Leu Pro Pro Leu
1               5                   10                  15

Glu Arg Leu Thr Leu Asp
            20

<210> SEQ ID NO 11
<211> LENGTH: 22
<212> TYPE: PRT
<213> ORGANISM: Artificial sequence
<220> FEATURE:
<223> OTHER INFORMATION: Designed antiviral peptide

<400> SEQUENCE: 11

Leu Pro Pro Leu Glu Arg Leu Thr Leu Asp Arg Gln Ala Arg Arg Asn
1               5                   10                  15

Arg Arg Arg Arg Trp Arg
            20

<210> SEQ ID NO 12
<211> LENGTH: 21
<212> TYPE: PRT
<213> ORGANISM: Artificial sequence
<220> FEATURE:
<223> OTHER INFORMATION: Designed antiviral peptide

<400> SEQUENCE: 12
```

```
Tyr Gly Arg Lys Lys Arg Arg Gln Arg Arg Leu Pro Pro Leu Glu
1               5                   10                  15

Arg Leu Thr Leu Asp
            20

<210> SEQ ID NO 13
<211> LENGTH: 16
<212> TYPE: PRT
<213> ORGANISM: Artificial sequence
<220> FEATURE:
<223> OTHER INFORMATION: Designed antiviral peptide

<400> SEQUENCE: 13

Arg Lys Lys Lys Arg Lys Val Leu Ala Leu Lys Ala Gly Leu Asp Ile
1               5                   10                  15

<210> SEQ ID NO 14
<211> LENGTH: 7
<212> TYPE: PRT
<213> ORGANISM: Homo sapiens

<400> SEQUENCE: 14

Arg Arg Met Lys Trp Lys Lys
1               5

<210> SEQ ID NO 15
<211> LENGTH: 7
<212> TYPE: PRT
<213> ORGANISM: Mus musculus

<400> SEQUENCE: 15

Arg Val His Pro Tyr Gln Arg
1               5

<210> SEQ ID NO 16
<211> LENGTH: 24
<212> TYPE: PRT
<213> ORGANISM: Homo sapiens

<400> SEQUENCE: 16

Lys Arg Pro Ala Cys Thr Leu Lys Pro Glu Cys Val Gln Gln Leu Leu
1               5                   10                  15

Val Cys Ser Gln Glu Ala Lys Lys
            20

<210> SEQ ID NO 17
<211> LENGTH: 7
<212> TYPE: PRT
<213> ORGANISM: Simian virus 40

<400> SEQUENCE: 17

Pro Lys Lys Lys Arg Lys Val
1               5

<210> SEQ ID NO 18
<211> LENGTH: 7
<212> TYPE: PRT
<213> ORGANISM: Saccharomyces cerevisiae

<400> SEQUENCE: 18

Gly Lys Lys Arg Ser Lys Ala
1               5

<210> SEQ ID NO 19
<211> LENGTH: 6
```

```
<212> TYPE: PRT
<213> ORGANISM: avian reticuloendotheliosis virus

<400> SEQUENCE: 19

Lys Ala Lys Arg Gln Arg
1               5

<210> SEQ ID NO 20
<211> LENGTH: 8
<212> TYPE: PRT
<213> ORGANISM: Rattus sp.

<400> SEQUENCE: 20

Arg Gly Arg Arg Arg Arg Gln Arg
1               5

<210> SEQ ID NO 21
<211> LENGTH: 5
<212> TYPE: PRT
<213> ORGANISM: Rattus sp.

<400> SEQUENCE: 21

Arg Lys Arg Arg Arg
1               5

<210> SEQ ID NO 22
<211> LENGTH: 9
<212> TYPE: PRT
<213> ORGANISM: Homo sapiens

<400> SEQUENCE: 22

Pro Pro Val Lys Arg Glu Arg Thr Ser
1               5

<210> SEQ ID NO 23
<211> LENGTH: 10
<212> TYPE: PRT
<213> ORGANISM: Saccharomyces cerevisiae

<400> SEQUENCE: 23

Pro Tyr Leu Asn Lys Arg Lys Gly Lys Pro
1               5                   10

<210> SEQ ID NO 24
<211> LENGTH: 17
<212> TYPE: PRT
<213> ORGANISM: Homo sapiens

<400> SEQUENCE: 24

Cys Tyr Gly Ser Lys Asn Thr Gly Ala Lys Lys Arg Lys Ile Asp Asp
1               5                   10                  15

Ala

<210> SEQ ID NO 25
<211> LENGTH: 9
<212> TYPE: PRT
<213> ORGANISM: Drosophila sp.

<400> SEQUENCE: 25

Lys Lys Lys Lys Arg Lys Arg Glu Lys
1               5

<210> SEQ ID NO 26
<211> LENGTH: 9
<212> TYPE: PRT
```

```
<213> ORGANISM: Drosophila sp.

<400> SEQUENCE: 26

Lys Lys Lys Arg Arg Ser Arg Glu Lys
1               5

<210> SEQ ID NO 27
<211> LENGTH: 18
<212> TYPE: PRT
<213> ORGANISM: Homo sapiens

<400> SEQUENCE: 27

Lys Val Thr Lys Arg Lys His Asp Asn Glu Gly Ser Gly Ser Lys Arg
1               5                   10                  15

Pro Lys

<210> SEQ ID NO 28
<211> LENGTH: 14
<212> TYPE: PRT
<213> ORGANISM: Rattus sp.

<400> SEQUENCE: 28

Lys Lys Lys Lys Lys Glu Glu Glu Gly Glu Gly Lys Lys Lys
1               5                   10

<210> SEQ ID NO 29
<211> LENGTH: 8
<212> TYPE: PRT
<213> ORGANISM: Borna disease virus

<400> SEQUENCE: 29

Pro Arg Pro Arg Lys Ile Pro Arg
1               5

<210> SEQ ID NO 30
<211> LENGTH: 13
<212> TYPE: PRT
<213> ORGANISM: Borna disease virus

<400> SEQUENCE: 30

Pro Pro Arg Ile Tyr Pro Gln Leu Pro Ser Ala Pro Thr
1               5                   10

<210> SEQ ID NO 31
<211> LENGTH: 20
<212> TYPE: PRT
<213> ORGANISM: Mus musculus

<400> SEQUENCE: 31

Lys Asp Cys Val Ile Asn Lys His His Arg Asn Arg Cys Gln Tyr Cys
1               5                   10                  15

Arg Leu Gln Arg
            20

<210> SEQ ID NO 32
<211> LENGTH: 11
<212> TYPE: PRT
<213> ORGANISM: Polyomavirus sp.

<400> SEQUENCE: 32

Ala Pro Lys Arg Lys Ser Gly Val Ser Lys Cys
1               5                   10

<210> SEQ ID NO 33
```

```
<211> LENGTH: 9
<212> TYPE: PRT
<213> ORGANISM: Human immunodeficiency virus

<400> SEQUENCE: 33

Arg Lys Lys Arg Arg Gln Arg Arg Arg
1               5

<210> SEQ ID NO 34
<211> LENGTH: 12
<212> TYPE: PRT
<213> ORGANISM: Human immunodeficiency virus

<400> SEQUENCE: 34

Arg Gln Ala Arg Arg Asn Arg Arg Arg Arg Trp Arg
1               5                   10

<210> SEQ ID NO 35
<211> LENGTH: 18
<212> TYPE: PRT
<213> ORGANISM: Homo sapiens

<400> SEQUENCE: 35

Met Pro Lys Thr Arg Arg Arg Pro Arg Arg Ser Gln Arg Lys Arg Pro
1               5                   10                  15

Pro Thr

<210> SEQ ID NO 36
<211> LENGTH: 17
<212> TYPE: PRT
<213> ORGANISM: Homo sapiens

<400> SEQUENCE: 36

Lys Arg Pro Met Asn Ala Phe Ile Val Trp Ser Arg Asp Gln Arg Arg
1               5                   10                  15

Lys

<210> SEQ ID NO 37
<211> LENGTH: 5
<212> TYPE: PRT
<213> ORGANISM: Homo sapiens

<400> SEQUENCE: 37

Arg Pro Arg Arg Lys
1               5

<210> SEQ ID NO 38
<211> LENGTH: 17
<212> TYPE: PRT
<213> ORGANISM: Homo sapiens

<400> SEQUENCE: 38

Lys Arg Pro Met Asn Ala Phe Ile Val Trp Ala Gln Ala Ala Arg Arg
1               5                   10                  15

Lys

<210> SEQ ID NO 39
<211> LENGTH: 5
<212> TYPE: PRT
<213> ORGANISM: Homo sapiens

<400> SEQUENCE: 39

Pro Arg Arg Arg Lys
1               5
```

```
<210> SEQ ID NO 40
<211> LENGTH: 4
<212> TYPE: PRT
<213> ORGANISM: Arabidopsis sp.

<400> SEQUENCE: 40

Arg Lys Arg Arg
1

<210> SEQ ID NO 41
<211> LENGTH: 9
<212> TYPE: PRT
<213> ORGANISM: Hepatitis C virus

<400> SEQUENCE: 41

Pro Pro Arg Lys Lys Arg Thr Val Val
1               5

<210> SEQ ID NO 42
<211> LENGTH: 13
<212> TYPE: PRT
<213> ORGANISM: epstein-barr virus

<400> SEQUENCE: 42

Tyr Lys Arg Pro Cys Lys Arg Ser Phe Ile Arg Phe Ile
1               5                   10

<210> SEQ ID NO 43
<211> LENGTH: 13
<212> TYPE: PRT
<213> ORGANISM: epstein-barr virus

<400> SEQUENCE: 43

Leu Lys Asp Val Arg Lys Arg Lys Leu Gly Pro Gly His
1               5                   10

<210> SEQ ID NO 44
<211> LENGTH: 5
<212> TYPE: PRT
<213> ORGANISM: adenovirus

<400> SEQUENCE: 44

Lys Arg Pro Arg Pro
1               5

<210> SEQ ID NO 45
<211> LENGTH: 5
<212> TYPE: PRT
<213> ORGANISM: Saccharomyces cerevisiae

<400> SEQUENCE: 45

Arg Lys Arg Lys Lys
1               5

<210> SEQ ID NO 46
<211> LENGTH: 7
<212> TYPE: PRT
<213> ORGANISM: Homo sapiens

<400> SEQUENCE: 46

Arg Arg Ser Met Lys Arg Lys
1               5

<210> SEQ ID NO 47
```

```
<211> LENGTH: 10
<212> TYPE: PRT
<213> ORGANISM: canine parvovirus

<400> SEQUENCE: 47

Pro Ala Lys Arg Ala Arg Arg Gly Tyr Lys
1               5                   10

<210> SEQ ID NO 48
<211> LENGTH: 17
<212> TYPE: PRT
<213> ORGANISM: Homo sapiens

<400> SEQUENCE: 48

Arg Lys Cys Leu Gln Ala Gly Met Asn Leu Glu Ala Arg Lys Thr Lys
1               5                   10                  15

Lys

<210> SEQ ID NO 49
<211> LENGTH: 17
<212> TYPE: PRT
<213> ORGANISM: Homo sapiens

<400> SEQUENCE: 49

Arg Arg Glu Arg Asn Lys Met Ala Ala Ala Lys Cys Arg Asn Arg Arg
1               5                   10                  15

Arg

<210> SEQ ID NO 50
<211> LENGTH: 17
<212> TYPE: PRT
<213> ORGANISM: Homo sapiens

<400> SEQUENCE: 50

Lys Arg Met Arg Asn Arg Ile Ala Ala Ser Lys Cys Arg Lys Arg Lys
1               5                   10                  15

Leu

<210> SEQ ID NO 51
<211> LENGTH: 17
<212> TYPE: PRT
<213> ORGANISM: Homo sapiens

<400> SEQUENCE: 51

Lys Lys Ser Lys Lys Gly Arg Gln Glu Ala Leu Glu Arg Leu Lys Lys
1               5                   10                  15

Ala

<210> SEQ ID NO 52
<211> LENGTH: 17
<212> TYPE: PRT
<213> ORGANISM: Homo sapiens

<400> SEQUENCE: 52

Arg Lys Glu Trp Leu Thr Asn Phe Met Glu Asp Arg Arg Gln Arg Lys
1               5                   10                  15

Leu

<210> SEQ ID NO 53
<211> LENGTH: 17
<212> TYPE: PRT
<213> ORGANISM: Homo sapiens
```

```
<400> SEQUENCE: 53

Lys Lys Gln Thr Thr Leu Ala Phe Lys Pro Ile Lys Lys Gly Lys Lys
1               5                   10                  15

Arg

<210> SEQ ID NO 54
<211> LENGTH: 17
<212> TYPE: PRT
<213> ORGANISM: Homo sapiens

<400> SEQUENCE: 54

Arg Lys Arg Lys Lys Met Pro Ala Ser Gln Arg Ser Lys Arg Arg Lys
1               5                   10                  15

Thr

<210> SEQ ID NO 55
<211> LENGTH: 23
<212> TYPE: PRT
<213> ORGANISM: Homo sapiens

<400> SEQUENCE: 55

Arg Ala Ile Lys Arg Arg Pro Gly Leu Asp Phe Asp Asp Asp Gly Glu
1               5                   10                  15

Gly Asn Ser Lys Phe Leu Arg
            20

<210> SEQ ID NO 56
<211> LENGTH: 7
<212> TYPE: PRT
<213> ORGANISM: Mus musculus

<400> SEQUENCE: 56

Arg Ile Arg Lys Lys Leu Arg
1               5

<210> SEQ ID NO 57
<211> LENGTH: 18
<212> TYPE: PRT
<213> ORGANISM: Homo sapiens

<400> SEQUENCE: 57

Lys Arg Ala Ala Glu Asp Asp Glu Asp Asp Val Asp Thr Lys Lys
1               5                   10                  15

Gln Lys

<210> SEQ ID NO 58
<211> LENGTH: 8
<212> TYPE: PRT
<213> ORGANISM: Homo sapiens

<400> SEQUENCE: 58

Gly Arg Lys Arg Lys Lys Arg Thr
1               5

<210> SEQ ID NO 59
<211> LENGTH: 13
<212> TYPE: PRT
<213> ORGANISM: Homo sapiens

<400> SEQUENCE: 59

Arg Glu Lys Lys Glu Lys Glu Gln Lys Glu Lys Cys Ala
1               5                   10
```

<210> SEQ ID NO 60
<211> LENGTH: 13
<212> TYPE: PRT
<213> ORGANISM: Homo sapiens

<400> SEQUENCE: 60

Leu Glu Lys Lys Val Lys Lys Phe Asp Trp Cys Ala
1               5                   10

<210> SEQ ID NO 61
<211> LENGTH: 7
<212> TYPE: PRT
<213> ORGANISM: Arabidopsis sp.

<400> SEQUENCE: 61

Arg Lys Arg Arg Thr Lys Lys
1               5

<210> SEQ ID NO 62
<211> LENGTH: 13
<212> TYPE: PRT
<213> ORGANISM: Thermoplasma acidophilum

<400> SEQUENCE: 62

Ser Asp Lys Lys Val Arg Ser Arg Leu Ile Glu Cys Ala
1               5                   10

<210> SEQ ID NO 63
<211> LENGTH: 7
<212> TYPE: PRT
<213> ORGANISM: avian neuroretina

<400> SEQUENCE: 63

Leu Lys Arg Lys Leu Gln Arg
1               5

<210> SEQ ID NO 64
<211> LENGTH: 7
<212> TYPE: PRT
<213> ORGANISM: Homo sapiens

<400> SEQUENCE: 64

Arg Arg Lys Gly Lys Glu Lys
1               5

<210> SEQ ID NO 65
<211> LENGTH: 13
<212> TYPE: PRT
<213> ORGANISM: Homo sapiens

<400> SEQUENCE: 65

Cys Lys Arg Lys Thr Thr Asn Ala Asp Arg Arg Lys Ala
1               5                   10

<210> SEQ ID NO 66
<211> LENGTH: 11
<212> TYPE: PRT
<213> ORGANISM: Homo sapiens

<400> SEQUENCE: 66

Val Asn Glu Ala Phe Glu Thr Leu Lys Arg Cys
1               5                   10

<210> SEQ ID NO 67
<211> LENGTH: 30

```
<212> TYPE: PRT
<213> ORGANISM: Zea mays

<400> SEQUENCE: 67

Met Pro Thr Glu Glu Arg Val Arg Lys Arg Lys Glu Ser Asn Arg Glu
1               5                   10                  15

Ser Ala Arg Arg Ser Arg Tyr Arg Lys Ala Ala His Leu Lys
            20                  25                  30

<210> SEQ ID NO 68
<211> LENGTH: 21
<212> TYPE: PRT
<213> ORGANISM: Rattus sp.

<400> SEQUENCE: 68

Lys Val Asn Ser Arg Lys Arg Lys Glu Val Pro Gly Pro Asn Gly
1               5                   10                  15

Ala Thr Glu Glu Asp
            20

<210> SEQ ID NO 69
<211> LENGTH: 6
<212> TYPE: PRT
<213> ORGANISM: Hepatitis C virus

<400> SEQUENCE: 69

Pro Arg Arg Gly Pro Arg
1               5

<210> SEQ ID NO 70
<211> LENGTH: 14
<212> TYPE: PRT
<213> ORGANISM: Hepatitis C virus

<400> SEQUENCE: 70

Pro Arg Gly Arg Arg Gln Pro Ile Pro Lys Ala Arg Gln Pro
1               5                   10

<210> SEQ ID NO 71
<211> LENGTH: 17
<212> TYPE: PRT
<213> ORGANISM: Homo sapiens

<400> SEQUENCE: 71

Lys Arg Ser Ala Glu Gly Gly Asn Pro Pro Lys Pro Leu Lys Lys Leu
1               5                   10                  15

Arg

<210> SEQ ID NO 72
<211> LENGTH: 11
<212> TYPE: PRT
<213> ORGANISM: Agrobacterium tumefaciens

<400> SEQUENCE: 72

Glu Tyr Leu Ser Arg Lys Gly Lys Leu Glu Leu
1               5                   10

<210> SEQ ID NO 73
<211> LENGTH: 20
<212> TYPE: PRT
<213> ORGANISM: Agrobacterium tumefaciens

<400> SEQUENCE: 73

Pro Lys Arg Pro Arg Asp Arg His Asp Gly Glu Leu Gly Gly Arg Lys
```

```
                1               5                  10                  15
Arg Ala Arg Gly
            20

<210> SEQ ID NO 74
<211> LENGTH: 16
<212> TYPE: PRT
<213> ORGANISM: Xenopus sp.

<400> SEQUENCE: 74

Lys Arg Pro Ala Ala Thr Lys Lys Ala Gly Gln Ala Lys Lys Lys Lys
1               5                  10                  15

<210> SEQ ID NO 75
<211> LENGTH: 18
<212> TYPE: PRT
<213> ORGANISM: Gallus gallus

<400> SEQUENCE: 75

Lys Arg Lys Lys Glu Met Ala Asn Lys Ser Ala Pro Glu Ala Lys Lys
1               5                  10                  15

Lys Lys

<210> SEQ ID NO 76
<211> LENGTH: 15
<212> TYPE: PRT
<213> ORGANISM: Homo sapiens

<400> SEQUENCE: 76

Tyr Asn Asn Gln Ser Ser Asn Phe Gly Pro Met Lys Gly Gly Asn
1               5                  10                  15

<210> SEQ ID NO 77
<211> LENGTH: 9
<212> TYPE: PRT
<213> ORGANISM: Homo sapiens

<400> SEQUENCE: 77

Pro Ala Ala Lys Arg Val Lys Leu Asp
1               5

<210> SEQ ID NO 78
<211> LENGTH: 17
<212> TYPE: PRT
<213> ORGANISM: Homo sapiens

<400> SEQUENCE: 78

Lys Arg Pro Ala Glu Asp Met Glu Glu Glu Gln Ala Phe Lys Arg Ser
1               5                  10                  15

Arg

<210> SEQ ID NO 79
<211> LENGTH: 13
<212> TYPE: PRT
<213> ORGANISM: Saccharomyces cerevisiae

<400> SEQUENCE: 79

Met Asn Lys Ile Pro Ile Lys Asp Leu Leu Asn Pro Gly
1               5                  10

<210> SEQ ID NO 80
<211> LENGTH: 7
<212> TYPE: PRT
<213> ORGANISM: Polyomavirus sp.
```

-continued

```
<400> SEQUENCE: 80

Pro Lys Lys Ala Arg Glu Asp
1               5

<210> SEQ ID NO 81
<211> LENGTH: 7
<212> TYPE: PRT
<213> ORGANISM: Polyomavirus sp.

<400> SEQUENCE: 81

Val Ser Arg Lys Arg Pro Arg
1               5

<210> SEQ ID NO 82
<211> LENGTH: 8
<212> TYPE: PRT
<213> ORGANISM: Simian virus 40

<400> SEQUENCE: 82

Ala Pro Thr Lys Arg Lys Gly Ser
1               5

<210> SEQ ID NO 83
<211> LENGTH: 7
<212> TYPE: PRT
<213> ORGANISM: Simian virus 40

<400> SEQUENCE: 83

Pro Asn Lys Lys Lys Arg Lys
1               5

<210> SEQ ID NO 84
<211> LENGTH: 12
<212> TYPE: PRT
<213> ORGANISM: Polyomavirus sp.

<400> SEQUENCE: 84

Glu Glu Asp Gly Pro Gln Lys Lys Lys Arg Arg Leu
1               5                   10

<210> SEQ ID NO 85
<211> LENGTH: 8
<212> TYPE: PRT
<213> ORGANISM: Homo sapiens

<400> SEQUENCE: 85

Pro Leu Leu Lys Lys Ile Lys Gln
1               5

<210> SEQ ID NO 86
<211> LENGTH: 8
<212> TYPE: PRT
<213> ORGANISM: Homo sapiens

<400> SEQUENCE: 86

Pro Pro Gln Lys Lys Ile Lys Ser
1               5

<210> SEQ ID NO 87
<211> LENGTH: 7
<212> TYPE: PRT
<213> ORGANISM: Homo sapiens

<400> SEQUENCE: 87
```

```
Pro Gln Pro Lys Lys Lys Pro
1               5

<210> SEQ ID NO 88
<211> LENGTH: 9
<212> TYPE: PRT
<213> ORGANISM: Homo sapiens

<400> SEQUENCE: 88

Ser Lys Arg Val Ala Lys Arg Lys Leu
1               5

<210> SEQ ID NO 89
<211> LENGTH: 10
<212> TYPE: PRT
<213> ORGANISM: Saccharomyces cerevisiae

<400> SEQUENCE: 89

Ile Lys Tyr Phe Lys Lys Phe Pro Lys Asp
1               5                   10

<210> SEQ ID NO 90
<211> LENGTH: 7
<212> TYPE: PRT
<213> ORGANISM: Saccharomyces cerevisiae

<400> SEQUENCE: 90

Lys Thr Arg Lys His Arg Gly
1               5

<210> SEQ ID NO 91
<211> LENGTH: 7
<212> TYPE: PRT
<213> ORGANISM: Saccharomyces cerevisiae

<400> SEQUENCE: 91

Lys His Arg Lys His Pro Gly
1               5

<210> SEQ ID NO 92
<211> LENGTH: 8
<212> TYPE: PRT
<213> ORGANISM: Homo sapiens

<400> SEQUENCE: 92

Pro Gln Ser Arg Lys Lys Leu Arg
1               5

<210> SEQ ID NO 93
<211> LENGTH: 9
<212> TYPE: PRT
<213> ORGANISM: Homo sapiens

<400> SEQUENCE: 93

Lys Lys Glu Lys Lys Lys Ser Lys Lys
1               5

<210> SEQ ID NO 94
<211> LENGTH: 8
<212> TYPE: PRT
<213> ORGANISM: Homo sapiens

<400> SEQUENCE: 94

Lys Arg Lys Lys Arg Arg His Arg
1               5
```